(12) United States Patent
Barthe et al.

(10) Patent No.: US 10,070,883 B2
(45) Date of Patent: *Sep. 11, 2018

(54) SYSTEMS AND METHOD FOR ULTRA-HIGH FREQUENCY ULTRASOUND TREATMENT

(71) Applicant: Guided Therapy Systems LLC, Mesa, AZ (US)

(72) Inventors: Peter G. Barthe, Phoenix, AZ (US); Michael H. Slayton, Mesa, AZ (US)

(73) Assignee: GUIDED THERAPY SYSTEMS, LLC, Mesa, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/334,988

(22) Filed: Oct. 26, 2016

(65) Prior Publication Data

US 2017/0043190 A1  Feb. 16, 2017

Related U.S. Application Data

(63) Continuation of application No. 13/914,945, filed on Jun. 11, 2013, which is a continuation of application
(Continued)

(51) Int. Cl.
*A61B 17/32* (2006.01)
*A61H 23/02* (2006.01)
(Continued)

(52) U.S. Cl.
CPC ........ *A61B 17/320068* (2013.01); *A61B 8/00* (2013.01); *A61H 23/0245* (2013.01);
(Continued)

(58) Field of Classification Search
CPC .... A61N 7/00; A61N 7/02; A61N 2007/0034; A61N 2007/0052; A61N 5/0616;
(Continued)

(56) References Cited

U.S. PATENT DOCUMENTS

| 5,295,484 | A | * | 3/1994 | Marcus | ............... | A61B 5/042 |
| | | | | | | 600/439 |
| 6,936,046 | B2 | * | 8/2005 | Hissong | ............... | A61N 7/02 |
| | | | | | | 601/2 |
| 7,070,565 | B2 | * | 7/2006 | Vaezy | ............... | A61B 8/4281 |
| | | | | | | 600/459 |

* cited by examiner

*Primary Examiner* — Peter Luong
(74) *Attorney, Agent, or Firm* — Quarles & Brady, LLP; James Schleicher

(57) ABSTRACT

A non-invasive ultra-high frequency ultrasound treatment method and system are provided. An exemplary method and system comprise a high-frequency ultrasound transducer system configured for providing ultrasound treatment to a patient such that the superficial and/or subcutaneous regions of the patient can be treated. An exemplary high-frequency ultrasound transducer system comprises a control system and a transducer configured to provide treatment to the superficial and/or subcutaneous regions of interest. The high-frequency ultrasound transducer may be configured to operate at higher frequencies and controlled power levels to provide treatment to the superficial and/or subcutaneous regions of interest. For example, higher frequencies within the range from approximately 20 MHz to 500 MHz or more may be utilized.

20 Claims, 3 Drawing Sheets

Related U.S. Application Data

No. 12/792,934, filed on Jun. 3, 2010, now Pat. No. 8,460,193, which is a continuation of application No. 11/245,999, filed on Oct. 6, 2005, now Pat. No. 7,758,524.

(60) Provisional application No. 60/616,356, filed on Oct. 6, 2004.

(51) Int. Cl.
*A61N 7/02* (2006.01)
*A61B 8/00* (2006.01)
*A61N 7/00* (2006.01)

(52) U.S. Cl.
CPC ........ *A61N 7/02* (2013.01); *A61N 2007/0034* (2013.01); *A61N 2007/0052* (2013.01)

(58) Field of Classification Search
CPC .............. A61B 8/00; A61B 2019/5276; A61B 17/320068; A61H 23/0245
See application file for complete search history.

SYSTEMS AND METHOD FOR ULTRA-HIGH FREQUENCY ULTRASOUND TREATMENT

CROSS-REFERENCE TO RELATED APPLICATIONS

This is a continuation application of U.S. patent application Ser. No. 13/914,945 filed Jun. 11, 2013, which is a continuation of U.S. patent application Ser. No. 12/792,934 filed Jun. 3, 2010, and issued as U.S. Pat. No. 8,460,193, which is a continuation of U.S. patent application Ser. No. 11/245,999 filed Oct. 6, 2005, and issued as U.S. Pat. No. 7,758,524, which claims priority to U.S. Provisional Patent Application 60/616,356 filed Oct. 6, 2004, all of which is incorporated in this application by reference.

FIELD OF INVENTION

This invention generally relates to an ultrasound system, and more particularly, to a method and system for ultra-high frequency ultrasound treatment.

BACKGROUND OF THE INVENTION

Many conventional applications of therapeutic ultrasound have employed low frequency transducers. These transducers have operational frequencies that typically range from 500 kHz to 1.5 MHz. Such low frequency transducers are often preferred because they allow for acoustical energy to be focused very deep into the body, without harming the overlying tissue structures.

A conventional application of non-invasive therapeutic ultrasound using a low-frequency transducer is depleted in FIG. 1. A conventional low-frequency therapeutic application 100 utilizes low frequency energy 102 to treat a deep treatment region 104, such as a deep-seated lesion. Deep treatment region 104 is located at a depth well below a superficial region of a patient. Use of the low-frequency transducer generates an isonified tissue region 106 that can range from 2 cm to 10 cm below the skin surface. Unfortunately, currently available low frequency transducers cannot be used to treat the superficial regions, thus limiting the use of low-frequency application 100. For example, most cosmetic surgeries, as well as treatment of melanomas and skin disorders, require treatment to superficial regions, thus eliminating the use of lower frequency transducers.

Another undesirable side effect of low-frequency therapy is that the acoustic energy must pass through intervening tissue layers before reaching the desired deep treatment area. The intervening layers tend to defocus the rays and absorb some of the acoustic energy. This causes the focal spot size to widen, making it difficult to control the location of the focal spot, and making dosimetry also difficult to optimize.

SUMMARY OF THE INVENTION

In accordance with various aspects of the present invention, a non-invasive ultra-high frequency ultrasound treatment method and system are provided. An exemplary method and system comprise an ultra-high frequency ultrasound transducer system configured for providing ultrasound treatment to a patient such that the superficial regions of the patient can be treated extracorporeally and internal tissues can he treated superficially in a minimally invasive fashion.

An exemplary ultra-high frequency ultrasound transducer system comprises a control system and a transducer configured to provide treatment to the superficial and/or internal superficial regions of interest. The ultra-high frequency ultrasound transducer may be configured to operate at higher frequencies and controlled power levels to provide safe, controlled treatment to superficial, and/or internal superficial tissue, e.g. an organ or tissue surface regions of interest. For example, higher frequencies within the range from approximately 20 MHz to 500 MHz or more may be utilized. In addition, by operating at optimum efficiency, the acoustic intensity can be suitably configured at high levels with the use of controlled, moderate power output levels. In accordance with an exemplary embodiment of the present invention, the ultra-high frequency ultrasound transducer can comprise a transduction element having a piezoelectrically active layer, matching layers and/or other materials for generating radiation or acoustical energy. The transduction element can comprise single or multiple elements.

In accordance with an exemplary embodiment of the present invention, the transduction element may be configured with an application device to facilitate coupling of the acoustical energy to the superficial and/or internal superficial regions of interest. The application device may be configured in various manners for coupling to the patient to provide treatment to the superficial and/or internal superficial regions of interest. In accordance with another exemplary embodiment, the transduction element may be configured on a minimally-invasive application device, such as a needle or other medical instrument, to permit the transduction element to come into substantially direct contact with various facia, e.g., the SMAS tissue layers, to facilitate treatment. Thus, instead of being placed on the outer surface of the skin, the application device may be inserted into the patient to come into more proximate acoustical contact with the targeted region for treatment.

In accordance with an exemplary embodiment of the present invention, an exemplary control system comprises a drive circuit and a feedback network configured to control the operation of the ultra-high frequency ultrasound transducer The drive circuit is configured to control power to the transduction element and can comprise various configurations, with and without voltage oscillation. In accordance with an exemplary embodiment, the drive circuit is configured to drive the frequency of the transduction element at the resonant frequency to facilitate maximum efficiency and/or maximum acoustic output. The feedback element is configured to use electrical signals front the driver circuit and/or the transduction element to facilitate control of the frequency of operation to provide optimum electro-acoustic conversion of energy. In addition, the control system can be suitably coupled to the transduction element in various manners.

In accordance with another aspect of the present invention, an ultra-high frequency ultrasound transducer system configured for providing ultrasound treatment to various depth regions within the superficial and/or internal superficial regions of the patient through control of the frequency of the transduction element and/or the cooling of the exemplary applicator device is provided.

BRIEF DESCRIPTION OF THE DRAWINGS

The subject matter of the invention is particularly pointed out and distinctly claimed in the concluding portion of the specification. The invention, however, both as to organization and method of operation, may best be understood by reference to the following description taken in conjunction with the claims and the accompanying drawing figures, in which like parts may be referred to by like numerals:

DETAILED DESCRIPTION

The present invention may be described herein in terms of various components and processing steps. It should be appreciated that such components and steps may be realized by airy number of hardware devices and components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical or treatment contexts and that the exemplary embodiments relating to ultra-high frequency ultrasound treatment as described herein are merely a few of the exemplary applications for the invention. For example, the principles, features and methods discussed may be applied to any medical or other tissue or treatment application.

In accordance with various aspects of the present invention, a non-invasive ultra-high frequency ultrasound treatment method and system are provided. An exemplary method and system comprise an ultra-high frequency ultrasound transducer system configured for providing ultrasound treatment to a patient such that superficial and/or internal superficial regions of a patient can be treated.

Figure 1:
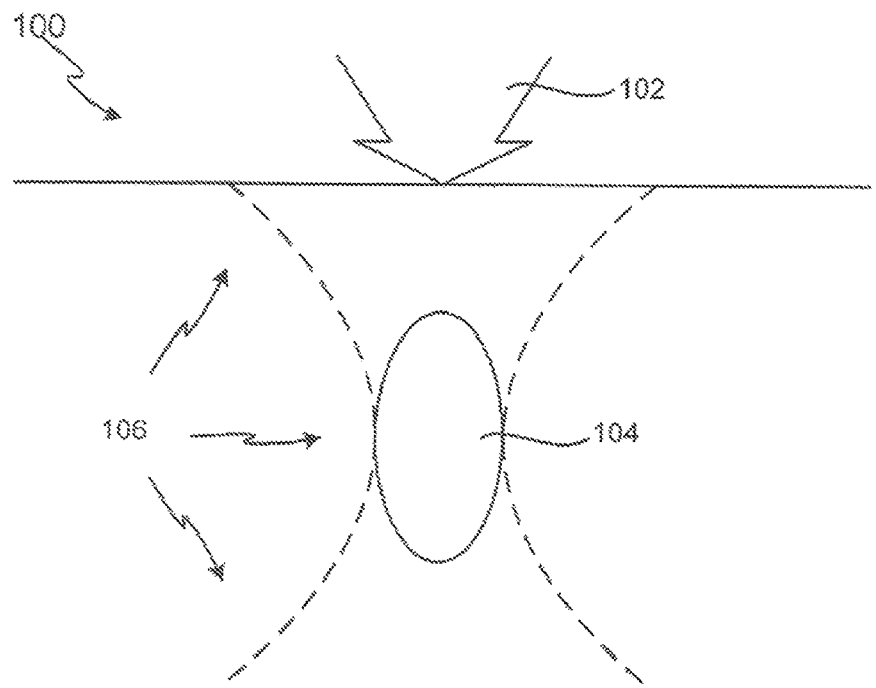
FIG. 1 illustrates a diagram of treatment application using a prior art low-frequency ultrasound treatment system.
Figure 2:
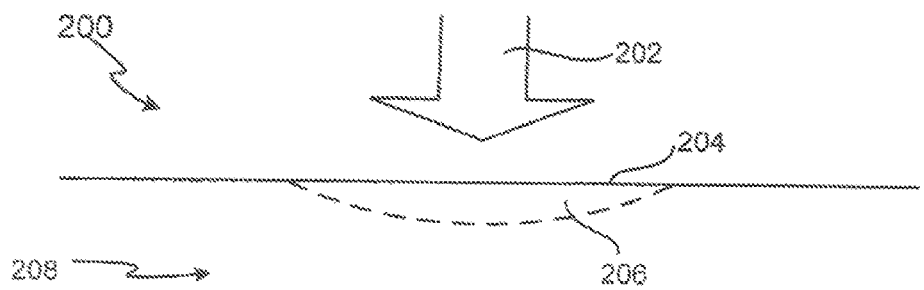
FIG. 2 illustrates a diagram of an ultra-high frequency ultrasound treatment application in accordance with an exemplary embodiment of the present invention.

With reference to FIG. 2 an exemplary ultra-high frequency ultrasound application 200 can comprise the applying of ultra-high frequency acoustical energy 202 to a superficial region 204 and/or internal superficial region 206 of a patient. Superficial region 204 comprises the skin layer of a patient, e.g., the outermost epidermis layer that can comprise between approximately 0.1 µm to 100 µm and the inner dermis layer between approximately 0.1 mm and 3 mm or more. The internal superficial region comprises the superficial layers of internal organs or tissue, for example between approximately 0 mm to 3 mm or more. Ultra-high frequency acoustical energy 202 is configured for operating at higher frequencies and suitable power levels such that the frequency dependent acoustic absorption provides treatment only at the superficial region 204 or internal superficial region.

For example, higher frequencies within the range from approximately 20 MHz to 500 MHz or more may be utilized to cause absorption within the regions of interest, such as within the epidermis layers and/or just below the dermis skin layers of the patient. Moreover, acoustic power levels may be configured to optimize the frequency dependent acoustic absorption at the ultra-high frequency levels to facilitate treatment to the regions of interest. By operating at optimum efficiency, the acoustic intensity can be suitably configured at high levels with the use of controlled, moderate power output levels. For example, for a steady-state ultrasound intensity of approximately 500 W/cm$^2$ at the outermost epidermis layer, the acoustical intensity can be configured to drop one to two orders of magnitude using the ultra-high frequencies, thus becoming highly absorbed as the energy penetrates the skin layers, e.g., at 300 MHz, the acoustical intensity drops to approximately 15 W/cm$^2$ at a depth of approximately 100 µm. As a result, the acoustic intensity is configured to be relatively large at the region of interest between superficial region 204 and treatment region 206, and then rapidly drop off to lower levels proximate to region 208. Accordingly, ultra-high frequency acoustical energy 202 can be used to suitably ablate superficial region 204, as well as internal superficial tissue and/or treat treatment region 206 whale leaving region 208 unaffected.

Figure 3:
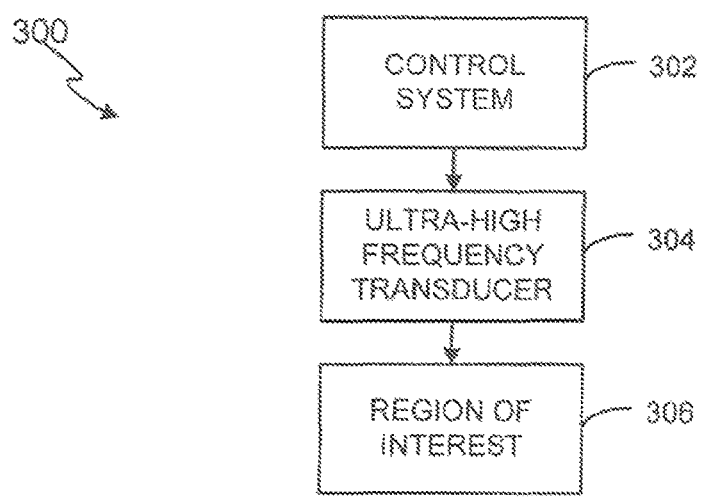
FIG. 3 illustrates a block diagram of an ultra-high frequency ultrasound treatment system in accordance with an exemplary embodiment of the present invention.

An exemplary high-frequency ultrasound transducer system can provide ultra-high frequency acoustical energy 202 in various configurations. For example, in accordance with an exemplary embodiment, with reference to FIG. 3, exemplary ultra-high frequency ultrasound system 300 comprises a control system 302 and a transducer 304 configured to provide treatment to a region of interest 306 within the superficial and/or internal superficial regions of a patient. In providing treatment, ultra-high frequency ultrasound system 300 may provide therapy, imaging and/or temperature monitoring to region of interest 306.

Control system 302 is configured for control and operation of transducer 304 to provide treatment. Control system 302 may comprise a processor, a display, and/or one or more input devices. In accordance with an exemplary embodiment, as discussed in more detail below, control system 302 can also comprise an electronic drive and control unit including a drive circuit, power supply and other electronic control devices that can be configured to drive the frequency of transducer 304 in a controlled manner for maximum efficiency. The processor may comprise a personal computer, a Unix system, or any other conventional processing unit. The display may comprise a monitor, LCD screen, or any other device configured to display an image. An input/output device may comprise a keyboard, a mouse, a touch-screen, or any other device for transmitting or receiving information to and from a control system. An "on/off" pushbutton or other control inputs may also be configured within control system 302. The information from the input device and images displayed may be received or transmitted in any format, such as manually, by analog device, by digital device, and/or by any other mechanisms.

The processor, display, electronic drive and control devices and/or input devices may be coupled together in any manner. By coupling, the devices comprising Control system 304 may be directly connected to each other or may be connected through one or more other devices or components that allow a signal to travel to/from one component to another. The various coupling components for the devices comprising control system 304 can include but are not limited to the internet, a wireless network, a conventional wire cable, an optical cable or connection through air, water, or any other medium that conducts signals, and any other coupling device or medium.

Transducer 304 is configured to operate at ultra-high frequencies. For example, frequencies within the range from approximately 20 MHz to 400 MHz or more may be selected to cause acoustic absorption within region of interest 306, i.e. within the outer epidermis layers, and/or just below the skin layers of the patient through the subcutaneous fat region. In accordance with an exemplary embodiment, transducer 304 can also be configured to operate at suitable power levels through control system 302 to provide a desired level of frequency dependent acoustic absorption. In accordance with an exemplary embodiment of the present invention, transducer 304 can comprise a transduction element having a piezoelectrically active layer, matching layers and/or other materials for generating radiation or acoustical energy that can be coupled to region of interest 306 in various manners.

Figure 4A:
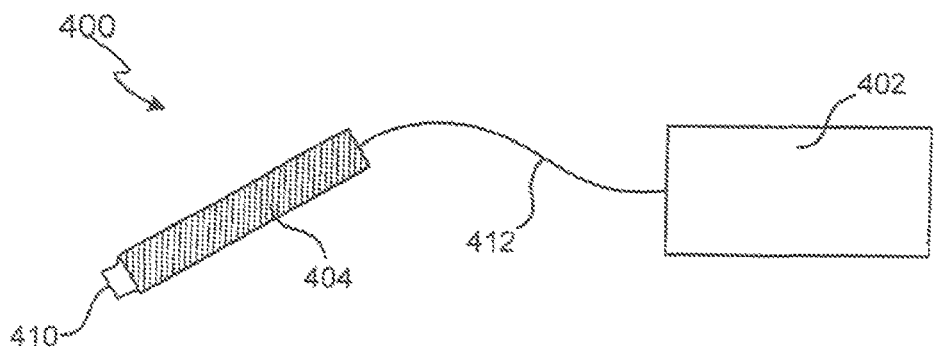
FIGS. 4A-4C illustrates a diagram of an ultra-high frequency ultrasound transducer system in accordance with an exemplary embodiment of the present invention.
Figure 4B:
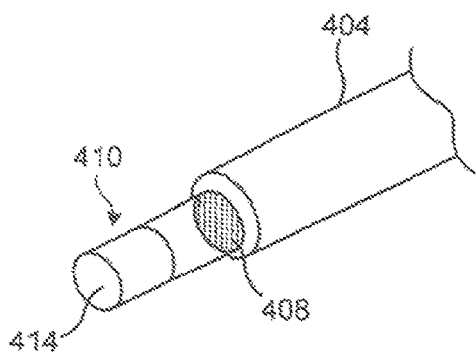
Figure 4C:
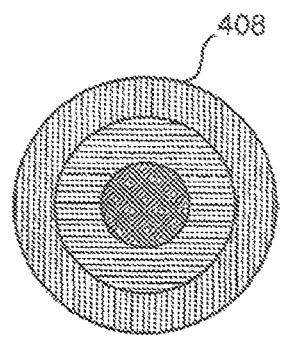

For example, with reference to FIGS. 4A-4C, in accordance with an exemplary embodiment of the present invention, an exemplary ultra-high frequency ultrasound system 400 comprises a control system 402 and a transducer 404. Control system 402 can comprise various circuit configurations for control of transducer 404, e.g., to provide drive signals to transducer 404. Control system 402 can also be coupled to transducer 404 in various manners, such as through a direct electrical connection through a cable 412, and/or through other coupling mechanisms, including capacitive coupling, thermo-acoustic coupling, and/or broadband, narrowband or high-pass acoustic filtering. Control system 402 can also be coupled to transducer 404 by inducing RF fields to transducer 404. For example, a periodic electric field can be polarized along the fully excited length of a transduction dement within transducer 404, such as along the x-axis of a X-cut rod of crystalline quartz or other crystal or piezoelectric element or polarized ferroelectrics material.

In accordance with an exemplary embodiment, transducer 404 comprises a housing 406, a transduction element 408 and an application device 410. Housing 406 is suitably configured to enclose or encapsulate components of transducer 404. Housing 406 can comprise any conventional housing or enclosure suitably for containing transducer elements and components, and can be shaped and sized in various manners. For example, in accordance with an exemplary embodiment housing 406 can be configured in the shape of a pen or stylus. However, housing 406 can be configured in any manner to allow for maneuvering and positioning of application device 410 along the skin surface of a patient.

Transduction element 408 can comprise a piezoelectrically active material, or any piezoelectric or polarized ferroelectric material, crystal, ceramic, plastic, and/or like composite materials. For example, transduction element 408 can comprise lead zirconante titanate (PZT), or any other piezoelectrically active material. Transduction element 408 can also comprise piezoelectric crystals, such as lithium niobate ($LiNbO_3$), lead titanate, barium titanate, quartz ($SiO_2$) and/or lead metaniobate, any polarized ferroelectric material, or any other crystals that possess low to very low dielectric and mechanical losses. Such elements and crystals can be suitably cut or shaped in various manners, such as Y-cut and X-cut configurations, e.g., an approximate 36-degree Y-cut lithium niobate crystal and an X-cut quartz crystal can exhibit excellent characteristics.

In addition to or instead of a piezoelectrically active material or crystals, transducer 404 may comprise any other materials configured for generating radiation and/or acoustical energy. Transducer 404 may also comprise one or more matching layers configured along with transduction element 408, e.g., coupled to the piezoelectrically active material, to optimize the acoustic output. For example, using matching layers designed for the fundamental resonant frequency of transduction element 408 can also cause matching of transduction element 408 at odd harmonic resonant frequencies as well. Any such matching layers can comprise thin films at higher frequencies, as opposed to thicker films used with low-frequency transducers that can vastly require an increase in acoustic power requirements.

The thickness of transduction element 408 of transducer 404 may be selected to provide a nominal or center operating frequency of a moderately high range, such as from approximately 10 MHz to 30 MHz or more, to facilitate greater resolution. For example, an approximately 4 mm diameter crystal, such as lithium niobate, having a 25 MHz nominal frequency can provide excellent efficiency, e.g., low dielectric losses, when operating at ultra-high frequencies, including within the range from approximately 20 MHz to 400 MHz or more. In addition, various crystalline materials can be suitably lapped in thickness to a high precision such that overtones, e.g., approximately odd harmonics, can be driven with high efficiency. Selecting the thickness of transduction element 408 and the resulting nominal frequency for operation cm be based on the degree and balance of energy penetration and resolution that is desired for a treatment application.

Transduction element 408 can comprise a single transduction element for generating acoustical energy. Transduction element 408 can also comprise multiple elements, such as that illustrated in FIG. 4C. For example, transduction element 408 can be suitably diced in a plurality of sections that can be suitably configured to focus on the treatment region at a certain depth and/or spot size within the region of interest. Transduction element 408 can be configured as multiple elements in various arrangements, such as that set forth in U.S. application Ser. No. 11/163,148, filed Oct. 6, 2005, entitled "Method and System for Controlled Thermal Injury," published as US 2006-0116671 on Jun. 1, 2006, and hereby incorporated by reference. In addition, a multiple element configuration for transduction element 408 can also be configured with electronic focusing to provide spot-size control. Electronic focusing can be implemented in various manners, such as that set forth in U.S. application Ser. No. 10/944,500, filed Sep. 16, 2004, entitled "System and Method for Variable Depth Ultrasound," published as US 2006-0058664 on Mar. 16, 2006, and hereby incorporated by reference.

Application device 410 is configured to facilitate coupling of the acoustical energy to a region of interest, such as to the superficial and/or internal superficial regions. In accordance with an exemplary embodiment application device 410 can comprise a standoff, a waveguide, or any other isolation/protection layer configured to enable transducer 404 to provide acoustical energy to the patient. Application device 410 can also comprise various sixes, shapes and configurations. For example, application device 410 can comprise a transparent, solid standoff such that a physician can precisely contact any small lesions in the epidermis region of the patient, and allow transducer 404 and application device 410 to be suitably sterilized tor further use. In addition, application device 410 can comprise a non-transparent disposable applicator tip, and/or an applicator tip that can be suitably replaced for different patients. Applicator device 410 can also be configured in various lengths, for example as a long waveguide of several millimeters, or as a shorter applicator tip of approximately 1 mm to a few hundred micrometers in length. Shorter lengths can allow for more efficient acoustic output as compared to longer lengths for a waveguide that can alter the frequency response of the transduction element 408/applicator device 410. In any event, the selection of length can be based upon the desired operating characteristics.

Applicator device 410 may be configured in various manners for coupling to the patient to provide treatment to the superficial anchor internal superficial regions of interest. For example, applicator device 410 can comprise materials and composites having very low acoustical losses, such as fused silica, or any other low loss materials. In addition, a tip 414 of applicator device 410 can comprise a substantially flat shape for coupling to the outer skin layer of a patient, a concave-like depression configured to focus acoustic energy to the region of interest, and/or an optical magnifier configured to visually magnify the outer skin layer of the patient as applicator device 410 is being coupled. Applicator device 410 can also be suitably coupled through a thin film of a low-loss coupling fluid, such as water or other commonly used coupling fluids for use with ultrasound transducers.

As discuss above, control system 402 can be configured in various manners for control of transducer 404. For example, control system 402 can comprise a processor, a display, and/or one or more input devices. Control system 402 can also comprise other devices and components, such power supplies, amplifiers, and/or filter devices. Such devices and components can be configured within a suitably electronic controls cabinet, housing or other enclosure. In accordance with an exemplary embodiment of the present invention, control system 402 comprises a drive circuit configured to control the operation of an exemplary ultra-high frequency ultrasound transducer.

An exemplary drive circuit can be configured in various manners. For example, with reference to FIG. 5A, a drive circuit 500 can comprise a driver 502 and a feedback network 504 configured in an oscillator-based, closed-loop arrangement to drive the frequency of transducer 404 in a controlled manner for maximum efficiency. In accordance with an exemplary embodiment, drive circuit 500 is configured to drive the frequency of the transduction element at the resonant frequency to facilitate maximum efficiency.

Driver 502 is configured to control power to a transduction element 506, e.g., a crystal or other suitable transduction element. Driver 502 can comprise various configurations. For example, driver 502 can comprise a power/oscillator driver, a linear power amplifier, or any other power source for providing power to drive a transduction element to create acoustical energy.

Feedback network 504 is configured to use electrical signals from driver circuit 502 and/or transduction element 506 to facilitate control of the frequency of operation, and thus provide optimum electro-acoustic conversion of energy. To maintain high electro-acoustical energy conversion efficiency, feedback network 504 can suitably facilitate control of the drive frequency to within a small fraction of the resonance frequency of transduction element 506.

Feedback network 504 comprises a closed-loop circuit, e.g., a self-oscillating or resonant circuit, to maintain the operating frequency of transduction element 506 in a manner that can enable optimum electro-acoustic conversion of energy. In other words, feedback network 504 is configured to cause driver circuit 502 to oscillate at the resonant frequency of frequency of transduction element 506, such as the frequency of crystal resonance. Feedback network 504 can create a 360-degree phase shift in the feedback loop of drive circuit 500. In addition, the configuration of feedback element 504 can provide a loop gain greater than or equal to one (1), thereby causing oscillation.

Figure 5A:
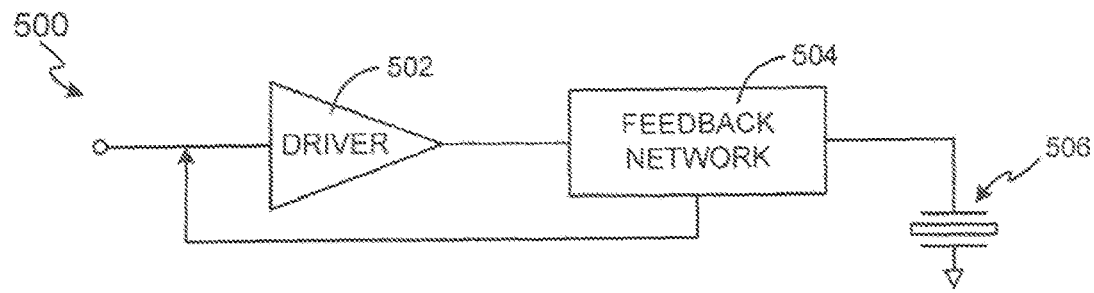
FIGS. 5A and 5B illustrate exemplary embodiments for control systems in accordance with the present invention.
Figure 5B:
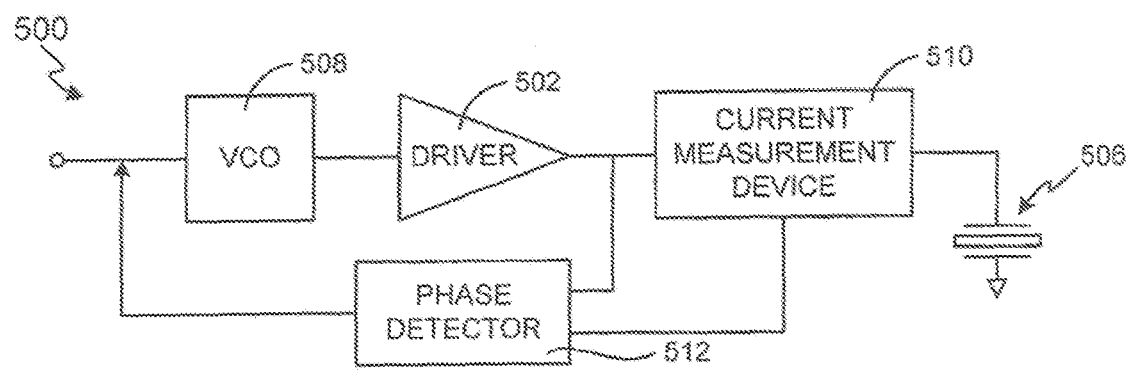

In addition to an oscillator-based drive circuit as illustrated in FIG. 5A, in accordance with another exemplary embodiment, with reference to FIG. 5B, drive circuit 500 can also comprise a voltage-controlled oscillator (VCO) based drive circuit. For example, drive circuit 500 can be configured with a power oscillator driver comprising driver 502 and a voltage-controlled oscillator (VCO) 508 and a feedback network comprising a current measurement device 510 and a phase detector 512. VCO 508 has an output signal coupled to the input of driver 502. VCO 508 can comprise any voltage-controlled oscillator circuit or device that can be configured to the nominal resonance frequency of the transduction element, e.g., the nominal resonance frequency of crystal 506. Current measurement device 510 can comprise one or more devices or components configured for measurement of the drive current from driver 502. For example, current measurement device 510 can comprise various current sensors, amplifiers or other measurement devices. Phase detector 512 is configured to receive voltage and current signals from driver 502 and current measurement device 510 and to provide a control signal to VCO 508. For example, since VCO 508 is configured to the resonance frequency of crystal 506, the current and voltage are in phase for crystal 506 since crystal tends to be resistive at the resonance frequency. However, when crystal 506 departs from the resonant frequency, the electrical impedance of crystal 506 becomes capacitive, and the current and voltage move out of phase. Thus, phase detector 512 can suitably measure the phases of the voltage and current and determine the phase differences to generate a correction voltage that can fine-tune the frequency of VCO 508 to the optimal frequency of oscillation.

Whether configured as an oscillator-based or VCO based drive circuit, or any other drive circuit configuration, drive circuit 500 can provide for high efficiency through electronic tuning, e.g., tracking of the optimal efficiency point, through use of a feedback network configured to facilitate control of the drive frequency to within a small fraction of the resonance frequency of transduction element 506. Since the resonant frequency of transduction elements can change due to loading, e.g., when application device 410 acoustically interfaces with the outer skin layers, drive circuit 500 can suitably control the drive frequency to thus maintain the optimum operating efficiency for a selected ultra-high frequency range of operation.

In addition, drive circuit 500 can be configured for driving transduction element 506 with either continuous waves of energy or short pulses of energy. Use of short pulses of energy can allow for an increase in the acoustic intensity level versus continuous waves of energy; however, drive circuit 500 is configured to make the acoustic intensity very large at the outer skin layers, e.g., the epidermis layer, and then have the acoustic intensity drop rapidly to lower levels, thus enabling continuous wave energy to also be used without detrimental effects to regions below the treatment regions of the patient. Moreover, by operating at optimum efficiency, the acoustic intensity can be suitably configured at high levels with use of moderate power output levels, e.g., a steady-state ultrasound intensity of approximately between 80 mW/cm$^2$ and 100 mW/cm$^2$ can cause sufficient but safe heating of the outer skin layer to facilitate treatment.

In accordance with mother aspect of the present invention, an exemplary ultra-high-frequency ultrasound transducer system can be configured for providing ultrasound treatment to various regions within the superficial and/or internal superficial regions of the patient. For example, the region of treatment can be suitably moved below the superficial region through control of the frequency of the transduction element by suitably decreasing the frequency from ultra-high frequency levels, e.g., 300 MHz or more, to extremely high frequency levels, e.g., 100 MHz.

In addition, the region of treatment can also be suitably moved below the superficial region through the cooling of the exemplary application device for the transducer. For example, with reference again to FIG. 4B, through controlled cooling of applicator lip 414, conductive cooling can occur at the outer skin surface, e.g., proximate the point of contact of application device 410 and the outer skin layer. Accordingly, applicator tip 414 and the outer skin surface can come into thermal equilibrium, thus sparing the outer skin layer from heating effects that are effectively "pushed" below the superficial region. Such controlled cooling can be utilized with and without additional frequency control to move the treatment region below the superficial region.

In accordance with an exemplary embodiment, closed-loop temperature control can be suitably utilized to actively control the temperature of applicator tip 414. For example, the cooling can be achieved through circulating water through a water-circulating member configured proximate to or within application tip 414, such as a thin non-absorbing membrane that can retain water and allow circulation. In accordance with other exemplary embodiments, the application device 410 can be configured with electrical-based cooling control to suitably control the temperature of applicator tip 414, such as through the use of thermoelectric modules, heat sinks. and/or temperature sensors and the like configured proximate to or within application tip 414. As a result of controlled cooling of the temperature of application device 410 and/or the controlling of frequency, the region of treatment can be suitably moved below the superficial region.

In accordance with another aspect of the present invention, an exemplary ultra-high frequency transducer system may be configured to enable energy deposition at not only a fundamental frequency of transduction element 408 of transducer 404, but also at corresponding subharmonic frequencies of the piezoelectric or other acoustically-active material as well. Energy is provided to a treatment region at its peak when a piezoelectrically active material is driven at its fundamental frequency. Different piezoelectric and/or other acoustically-active materials have different fundamental frequencies. In accordance with an exemplary embodiment, energy can also be deposited at smaller peaks, i.e., at subharmonic frequencies, when the piezoelectric material is driven at its fundamental frequency. The use of the subharmonic characteristics of transducer 404 may be controlled and enabled through various focusing techniques.

Figure 6:
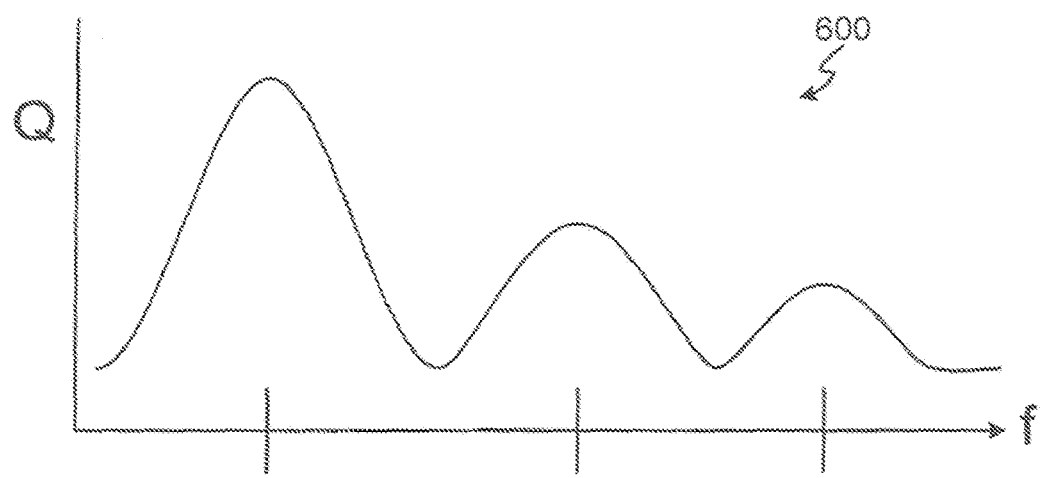
FIG. 6 illustrates an exemplary diagram of treatment characteristics of an exemplary transducer operating at the fundamental frequency and subharmonics in accordance with the present invention.

In accordance with an exemplary embodiment, enablement of the harmonics allows for treatment at various depths corresponding to the different harmonics. For example, with additional reference to frequency-harmonics curve illustrated in FIG. 6, ultra-high frequency transducer system 400 may treat various regions within the superficial and/or internal superficial regions of the patient, as represented by curve 600. Driving harmonic frequencies through transducer 404 enables treatment of a first superficial region, treatment of a second shallower region just below the former region, etc.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the method and system for ultra-high frequency ultrasound treatment with a transducer is described above is suitable for use by a medical practitioner proximate the patient, the control system can also be accessed remotely, i.e., the medical practitioner can view and/or operate the control system through a remote display or otter remote I/O devices having imaging information transmitted in various manners of communication, such as by satellite/wireless or by wired connections such as IP or digital cable networks and the like, and can direct a local practitioner as to the suitably placement for the transducer. These and other changes or modifications are intended to be included within the scope of the present invention, as set forth in the following claims.

The invention claimed is:

1. A method for providing treatment to a patient having a melanoma or a non-melanoma skin disorder, the method comprising:
coupling an ultrasound transducer to a skin surface of a patient;
emitting energy from the ultrasound transducer in a frequency range from about 10 MHz to about 30 MHz or from about 20 MHz to about 500 MHz into a superficial region of interest below the skin surface of the patient, the superficial region of interest consisting of a subcutaneous layer of skin,
thereby ablating tissue in a portion of the region of interest,
thereby creating a lesion in the tissue at a depth in a range of 0.1 μm to 100 μm below the skin surface, the lesion treating the melanoma or the non-melanoma skin disorder; and
sparing tissue at the depth of greater than 100 μm below the skin surface from damage from the ablating tissue.

2. The method according to claim 1, wherein the subcutaneous layer of skin comprises an epidermis layer.

3. The method according to claim 1, further comprising imaging at least a portion of the superficial region of interest; and displaying the at least a portion of the superficial region of interest.

4. The method according to claim 1, wherein the emitting energy from the ultrasound transducer is in a power range of 80 W/cm$^2$ to 100 W/cm$^2$.

5. The method according to claim 1, wherein the emitting energy from the ultrasound transducer is in a power range of 15 W/cm$^2$ to 500 W/cm$^2$.

6. The method according to claim 5, wherein the emitting energy from the ultrasound transducer is in a power range of about 500 W/cm$^2$ at a depth of about 0.1 μm below the skin surface.

7. The method according to claim 5, wherein the emitting energy from the ultrasound transducer is in a power range of about 15 W/cm$^2$ at a depth of about 100 μm below the skin surface.

8. The method according to claim 1, wherein the emitting energy from the ultrasound transducer is in a frequency range from about 20 MHz to about 500 MHz.

9. The method according to claim 1, wherein the emitting energy from the ultrasound transducer is in a frequency range from about 10 MHz to about 30 MHz.

10. A method for treating a melanoma in a patient's skin, the method comprising:

coupling an ultrasound transducer to a skin surface of the patient;

emitting energy from the ultrasound transducer within a frequency range from about 10 MHz to about 30 MHz into a region of interest comprising superficial tissue in at a depth in a range of 0.1 µm to 100 µm below the skin surface;

ablating superficial tissue in a portion of the region of interest;

creating a lesion in the superficial tissue;

treating a melanoma in the region of interest; and leaving tissue below the region of interest unaffected.

11. The method according to claim 10, farther comprising imaging at least a portion of the melanoma in the region of interest; and displaying an image of the portion of the melanoma.

12. The method according to claim 10, wherein the emitting energy from the ultrasound transducer is in a power range of 80 W/cm$^2$ to 100 W/cm$^2$.

13. The method according to claim 10, wherein the emitting energy from the ultrasound transducer is in a power range of 15 W/cm$^2$ to 500 W/cm$^2$.

14. The method according to claim 13, wherein the emitting energy from the ultrasound transducer is in a power range of about 500 W/cm$^2$ at a depth of about 0.1 µm below the skin surface.

15. The method according to claim 13, wherein the emitting energy from the ultrasound transducer is in a power range of about 15 W/cm$^2$ at a depth of about 100 µm below the skin surface.

16. A method for providing ultrasound treatment to a patient having a melanoma or a non-melanoma skin disorder, the method comprising:

a) operating a transducer to emit acoustical energy within a frequency range from about 10 MHz to 30 MHz or from about 20 MHz to about 500 MHz;

b) coupling the transducer to a region of interest consisting of a superficial region and a subcutaneous region;

c) focusing a first acoustical energy to a first depth in the region of interest, thereby ablating a portion of superficial tissue in the superficial region, thereby creating a first lesion in the superficial tissue;

d) focusing a second acoustical energy to a second depth in the region of interest, thereby ablating a portion of subcutaneous tissue in the subcutaneous region, thereby creating a second lesion in the subcutaneous tissue; and e) leaving tissue below the region of interest unaffected, wherein the focusing of step c), step d), or steps c) and d) treats the melanoma or the non-melanoma skin disorder in at least a portion of the region of interest.

17. The method according to claim 16, wherein the superficial region is at a depth in a range of 0.1 µm to 100 µm below a skin surface and the subcutaneous region is at a depth in a range of 100 µm to 3 mm below the skin surface.

18. The method according to claim 16, wherein the first acoustical energy and the second acoustical energy is within the frequency range from about 10 MHz to about 30 MHz.

19. The method according to claim 16, wherein the first acoustical energy and the second acoustical energy is in a power range of 15 W/cm$^2$ to 500 W/cm$^2$.

20. The method according to claim 16, the patient having the non-melanoma skin disorder, wherein the focusing of step c), step d), or steps c) and d) treats the non-melanoma skin disorder in at least a portion of the region of interest.

* * * * *

UNITED STATES PATENT AND TRADEMARK OFFICE
CERTIFICATE OF CORRECTION

PATENT NO. : 10,070,883 B2
APPLICATION NO. : 15/334988
DATED : September 11, 2018
INVENTOR(S) : Peter G. Barthe et al.

It is certified that error appears in the above-identified patent and that said Letters Patent is hereby corrected as shown below:

In the Specification

Column 1, Line 33, "depleted" should be --depicted--.

Column 1, Line 62, "he" should be --be--.

Column 2, Line 47, "front" should be --from--.

Column 3, Line 27, "airy" should be --any--.

Column 4, Line 21, "whale" should be --while--.

Column 5, Line 29, "dement" should be --element--.

Column 6, Line 22, "cm" should be --can--.

Column 6, Line 53, "sixes" should be --sizes--.

Column 7, Line 6, "anchor" should be --and/or--.

Column 8, Line 62, "mother" should be --another--.

Column 9, Line 9, "lip" should be --tip--.

Column 10, Line 8, "tor" should be --for--.

Column 10, Line 12, "otter" should be --other--.

Signed and Sealed this
Thirteenth Day of November, 2018

Andrei Iancu
*Director of the United States Patent and Trademark Office*